(12) United States Patent
Sharma et al.

(10) Patent No.: US 11,342,080 B2
(45) Date of Patent: May 24, 2022

(54) METHOD AND SYSTEM FOR DISEASE PROGRESSION MODELING AND THERAPY OPTIMIZING FOR INDIVIDUAL PATIENTS

(71) Applicant: Siemens Healthcare GmbH, Erlangen (DE)

(72) Inventors: Puneet Sharma, Monmouth Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 459 days.

(21) Appl. No.: 15/745,729

(22) PCT Filed: Aug. 17, 2016

(86) PCT No.: PCT/EP2016/069490
§ 371 (c)(1),
(2) Date: Jan. 18, 2018

(87) PCT Pub. No.: WO2017/029314
PCT Pub. Date: Feb. 23, 2017

(65) Prior Publication Data
US 2018/0233233 A1    Aug. 16, 2018

Related U.S. Application Data

(60) Provisional application No. 62/205,877, filed on Aug. 17, 2015.

(51) Int. Cl.
*G01N 33/48* (2006.01)
*G01N 33/50* (2006.01)
(Continued)

(52) U.S. Cl.
CPC ............. *G16H 50/50* (2018.01); *G16H 50/20* (2018.01); *G16H 50/30* (2018.01); *A61B 5/4842* (2013.01); *G16H 20/00* (2018.01)

(58) Field of Classification Search
CPC ........ G16H 50/50; G16H 50/30; G16H 50/20; G16H 20/00; A61B 5/4842
See application file for complete search history.

(56) References Cited

U.S. PATENT DOCUMENTS 8,019,553 B1    9/2011  Goldstein
8,494,871 B2    7/2013  Schaffer et al.
(Continued)

FOREIGN PATENT DOCUMENTS

CN    101743552 A    6/2010
CN    102713914 A    10/2012
(Continued)

OTHER PUBLICATIONS

Singh et al. Gene expression correlates of clinical prostate cancer behavior. Cancer Cell, vol. 1, pp. 203-209. (Year: 2002).*
(Continued)

*Primary Examiner* — Russell S Negin (57) ABSTRACT

A method and system for automated disease progression modeling and therapy optimization for an individual patient is disclosed. A current condition of the patient is modeled using a state-variable model in which a plurality of state variables in a state vector represent a plurality of characteristics of the patient. Disease progression for the patient is predicted based on the state variables of the patient. An optimization is performed to determine an optimal therapy type and an optimal therapy timing for the patient based on the predicted disease progression for the patient.

21 Claims, 7 Drawing Sheets

(51) Int. Cl.
*G16H 50/50* (2018.01)
*G16H 50/30* (2018.01)
*G16H 50/20* (2018.01)
*G16H 20/00* (2018.01)
*A61B 5/00* (2006.01)

(56) References Cited

U.S. PATENT DOCUMENTS

| | | |
|---|---|---|
| 8,862,448 B2 | 10/2014 | Holmes et al. |
| 9,953,139 B2 | 4/2018 | Lapraz |
| 2002/0155422 A1 | 10/2002 | Ingber et al. |
| 2007/0015837 A1* | 1/2007 | Kun ............ A61K 31/166 514/621 |
| 2010/0191071 A1 | 7/2010 | Anderson et al. |
| 2010/0280352 A1 | 11/2010 | Ionasec et al. |
| 2011/0313790 A1 | 12/2011 | Yao |
| 2012/0022840 A1 | 1/2012 | O'Neil |
| 2012/0053911 A1* | 3/2012 | Torres-Roca ............ G16B 5/00 703/2 |

FOREIGN PATENT DOCUMENTS

| | | |
|---|---|---|
| CN | 102947857 A | 2/2013 |
| CN | 103180856 A | 6/2013 |

OTHER PUBLICATIONS

International Search Report dated Nov. 29, 2016 in corresponding International Application No. PCT/EP2016/069490.

Ahmed Abbas Suleiman et al: "Modelling NSCLC Progression: Recent Advances and Opportunities Available", The AAPS Journal, vol. 15, No. 2, Apr. 2013, pp. 542-550.

Yuanxi Li et al: "Modelling and analysing the dynamics of disease progression from cross-sectional studies", Journal of Biomedical Informatics, vol. 46, No. 2, 2013, pp. 266-274.

Michael Lawton et al: "A longitudinal model for disease progression was developed and applied to multiple sclerosis", Journal of Clinical Epidemiology, vol. 68, No. 11, 2015, pp. 1355-1365.

Tiemann, et al: "Parameter Trajectory Analysis to Identify Treatment Effects of Pharmacological Interventions," PLOS Computational Biology, Aug. 2013.

Liberzon, D.: "Switching in Systems and Control"; Birkhauser 2003; DOI: 10.1007/978-1-4612-0017-8 ISBN: 9781461200178.

Johnson, et al: "Prognostic Value of Fractional Flow Reserve: Linking Physiologic Severity to Clinical Outcomes," Journal of the American College of Cardiology, vol. 64, Issue 16, 2014.

* cited by examiner

METHOD AND SYSTEM FOR DISEASE PROGRESSION MODELING AND THERAPY OPTIMIZING FOR INDIVIDUAL PATIENTS

This application claims the benefit of U.S. Provisional Application No. 62/205,877, filed Aug. 17, 2015, the disclosure of which is herein incorporated by reference.

BACKGROUND OF THE INVENTION

The present invention relates to predictive modeling of disease progression, and more particularly, to modeling disease progression and optimizing a time and type of therapy for individual patients.

Disease progression for many types of diseases is often characterized by a number of variables ranging from qualitative measures (often determined by patients or clinicians based on the patient's answers to standard questions) to more quantitative measures, such as diagnostic tests, in-vivo measurements, medical imaging, etc. A clinician considers this information from heterogeneous sources, and based on this information, the clinician decides a placement of the patient at a specific spot along the disease projection trajectory. This placement is then used by the clinician to determine a recommended therapeutic strategy for the patient, which could range from "do nothing", to drug therapy, to more invasive device-based therapy.

BRIEF SUMMARY OF THE INVENTION

The present invention provides a method and system for disease progression modeling and therapy optimization for individual patients. Embodiments of the present invention utilize a system theoretic framework to model the disease progression of an individual patient or a group of patients based on various patient characteristics that are identified by multiple diagnostic tests. Embodiments of the present invention also incorporate the effects of interventions on the disease progression model, which can then be used to identify an optimal type and timing of an intervention to treat an individual patient.

In one embodiment of the present invention, a current condition of the patient is modeled using a state-variable model in which a plurality of state variables in a state vector represent a plurality of characteristics of the patient. Disease progression for the patient is predicted based on the state variables of the patient. An optimization is performed to determine an optimal therapy type and an optimal therapy timing for the patient based on the predicted disease progression for the patient.

These and other advantages of the invention will be apparent to those of ordinary skill in the art by reference to the following detailed description and the accompanying drawings.

DETAILED DESCRIPTION

The present invention relates to a method and system for disease progression modeling and therapy optimization for individual patients. Embodiments of the present invention also incorporate the effects of interventions on the disease progression model, which can then be used to identify an optimal type and timing of an intervention to treat an individual patient. Embodiments of the present provide automated predicted of disease progression trajectories and automated optimization to identify the optimal type and timing of treatment for the patient.

Figure 1:
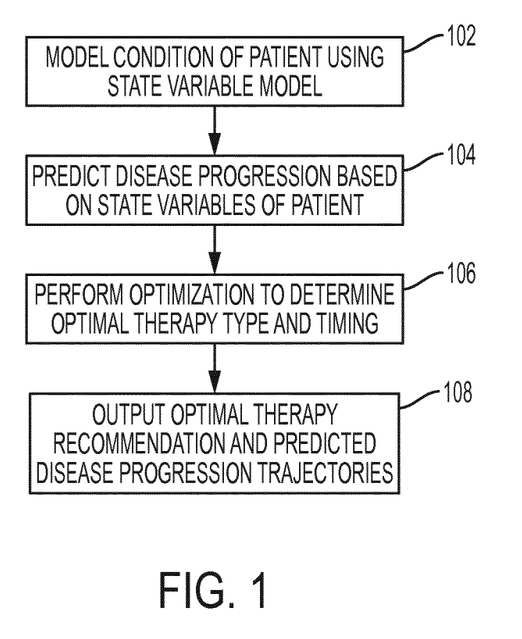
FIG. 1 illustrates a method of disease projection modeling and therapy optimization for an individual patient according to an embodiment of the present invention.

FIG. 1 illustrates a method of disease projection modeling and therapy optimization for an individual patient according to an embodiment of the present invention. At step 102, the condition of a patient is modeled using a state variable model. The current condition of a patient is characterized internally by a set of state variables. These state variables are intrinsic to the system and will evolve over time as the patient's condition changes (i.e., worsens, stays the same, or improves). The vector of these state variables is referred to as the state vector of the patient and is used to characterize the current state of the patient.

The state variables may represent information from multiple biological scales, such as various measurements at the cellular, tissue, organ, and/or system level. In addition to such physiological data, other data characterizing the patient such as demographic data, such as age, sex, family history, etc. can also be included in the state vector. The time varying state vector is represented by x(t):

$$x(t) = \begin{bmatrix} x_1(t) \\ x_2(t) \\ \cdots \\ \cdots \\ \cdots \\ x_N(t) \end{bmatrix}$$

The evolution of the state variables system can be modeled by linear or non-linear differential equations. These differential equations can be deterministic or stochastic equations. The differential equations that model the evolution of each state variable x(t) can be expressed as:

$$\dot{x}(t) = f(x(t), u(t)$$

$$y(t) = g(x(t), u(t)),$$

where f( ) and g( ) are either linear of non-linear functions, and y(t) is the measurement at time t.

Values for state variables representing various physiological measurements for a patient can be acquired in various ways. For example various state variables may be determined from non-invasive measurements of the patient can be acquired, such as blood pressure, heart rate, weight, etc., medical images of the patient, such as magnetic resonance imaging (MRI), computed tomography (CT), X-ray, Ultrasound, etc., blood tests, other routine physical tests, and invasive physiological measurements, such as measurements acquired during a surgical or transcatheter procedure. Image processing techniques may be used to determine various anatomical and physiological measurements from medical imaging data of the patient. For example: In heart failure cases, the heart function can be characterized by various anatomical and functional measurements from medical images, such as ejection fraction, cardiac output, shape/size of the 4 cardiac chambers in 2D, 3D or 4D, myocardial mass, flow across the 4 valves, pressure measurements in the chambers or in the vessels, myocardial mass and volumes, myocardial strain, myocardial perfusion values such as blood flow and blood volume, tissue characterization (T1, T2 and T2* values from MRI), etc. These state variables can be determined by using image processing algorithms that automatically detect, extract and quantify some or all of these measurements from one or more medical images for a given individual. Alternatively, some or all of these state variables can be manually or semi-automatically extracted from one or more medical images by a human (e.g., a radiologist, a cardiologist, a technologist etc.).

Not all of these state variables can be measured accurately by the routinely available sensing devices. As a result, it cannot be assumed that the state vector can be fully resolved at all times. For example: in the case of heart failure, cardiac imaging (such as MRI, CT, Ultrasound, X-ray angiography or nuclear imaging—SPECT/PET), blood based biomarker, and routine physical tests are routinely administered to the patients. In such patients, cardiac imaging can be used to characterize the various cardiac function parameters such as ejection fraction, end-systolic and end-diastolic volumes, regurgitant fractions etc., by applying various image processing techniques. Additional invasive measurements may also be available, such as left ventricle (LV) and aortic pressure traces, to further add to the list of measurements. However, all of these measurements together may not be enough to fully characterize the current state of the patient's heart.

Given a set of measurement data (at a given point in time or over multiple points in time) resulting from imaging and non-imaging measurements for a patient, a dynamical system identification algorithm may be used to estimate the parameters of the dynamical system. Such a dynamical system identification algorithm uses statistical methods to estimate unknown parameters and hidden states of the dynamical system from the available measured data. The dynamical system identification algorithm can be applied even in cases in which there are missing state values and/or noisy values for some attributes. Any type of dynamical system identification algorithm may be used. For example, neural networks and deep learning methods for system identification may be used, but the present invention is not limited thereto.

At step 104, disease progression is predicted for the patient based on the state variables of the patient. The disease progression is modeled by predicting how the state variables evolve over time. Certain state variables, such as tumor size, cardio blood biomarkers, fraction flow reserve, etc., act as indicators for how particular diseases evolve. The evolution of state variables characterizing a certain disease over time is considered to be the disease trajectory for a patient. The future evolution of the state variables and disease trajectory is predicted based on current values of the state variables and/or an observed trajectory of the state variables over an initial time period.

In one embodiment, a comprehensive set of disease trajectories from different patients may be used to estimate a typical disease trajectory for a particular subgroup of patients. A database of disease trajectories for a large number of different patients can be compiled. In particular, the state variable values over a period of time are stored for each patient. Instead of estimating the typical disease trajectory over the entire population of the patients in the database, a sub-group analysis is performed, where the sub-group may be selected by considering certain characteristics of the state vector. A typical disease trajectory can then be estimated for the sub-group, for example, by averaging the disease trajectories of the subgroup. For example, an age-based sub-group (e.g., patients between the ages of 50-60 years) may be identified and then a typical disease trajectory for such a sub-group can be estimated. Another example may be cardiac patients with an ejection fraction between 30-40%. Yet another example can be a sub-group of cardiac patients with a calcium score (Agatston score) over/under a certain prescribed threshold. Sub-groups may also be defined using multiple state variables from the state vector. For example, in the case of heart failure, one sub-group can be patients with an ejection fraction below 30% and QRS duration on the ECG>120 ms. The state variable or combination of state variables used to define the subgroups can be preset for particular diseases, and then the sub-group analysis can be automatically performed in order to predict the disease trajectory for the patient by estimating the typical disease projector of the corresponding sub-group. It is also possible that a user can define the sub-group by inputting the state variable or combination of state variables that define the sub-group, and the sub-group analysis can then be automatically performed in response to receiving the input defining the sub-group. In addition to determining a typical (e.g., average) disease trajectory of the sub-group, other disease trajectories can also be determined from the sub-group, such as a best-case disease trajectory for the sub-group and a worst-case disease trajectory for the sub-group.

Figure 2:
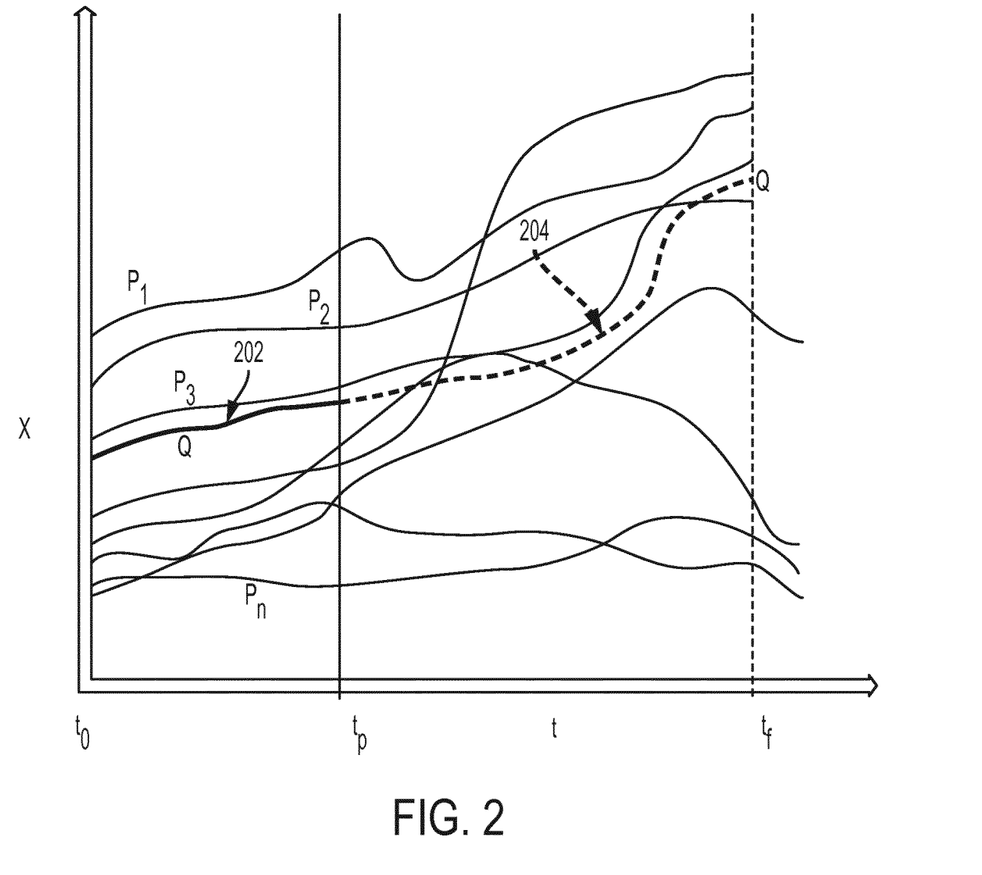
FIG. 2 illustrates disease progression modeling using trajectory clustering according to an embodiment of the present invention.

In another embodiment, the prediction of the disease progression for the patient based on the state variable can be performed using a trajectory clustering algorithm. In particular, a trajectory clustering algorithm can be used to group the database of disease trajectories into several clusters. A difference metric, such as the Euclidean norm, is used to compare the current state vector of the patient or an initial disease trajectory defined by the state vector values over an initial time period to the clusters in the database to and assign the current patient to one of the clusters by finding the most similar cluster. The patient's disease trajectory is then determined using the average disease trajectory for the assigned cluster in the database of disease trajectories. FIG. 2 illustrates disease progression modeling using trajectory clustering according to an embodiment of the present invention. As shown in FIG. 2, $P_1$, $P_2$, $P_3$, . . . , $P_n$ are average disease trajectories for clusters 1-$n$ in a database of disease trajectories. It can be noted that in the trivial case, the trajectories $P_1$, $P_2$, $P_3$, . . . , $P_n$ may represent clusters of size 1, i.e., individual patients rather than a group of patients, but in an advantageous implementation each of these trajectories represents a cluster of multiple patients. Q represents the patient's disease trajectory, with 202 being the known initial disease trajectory between $t_0$ and $t_p$, and 204 being the predicted disease trajectory between $t_p$ and $t_f$. The initial disease trajectory 202 of Q is compared to the initial portions of $P_1$-$P_n$, and it the most similar cluster to Q is determined to be $P_3$. In order to estimate the predicted disease trajectory 204 of Q, the evolution of the state variables in Q between $t_p$ and $t_f$ match the evolution of the state variables in $P_3$ between $t_p$ and $t_f$. For the trajectory clustering, the whole state vector or some predefined subset of state variables in the state vector may be used to find the most similar cluster.

Figure 3:
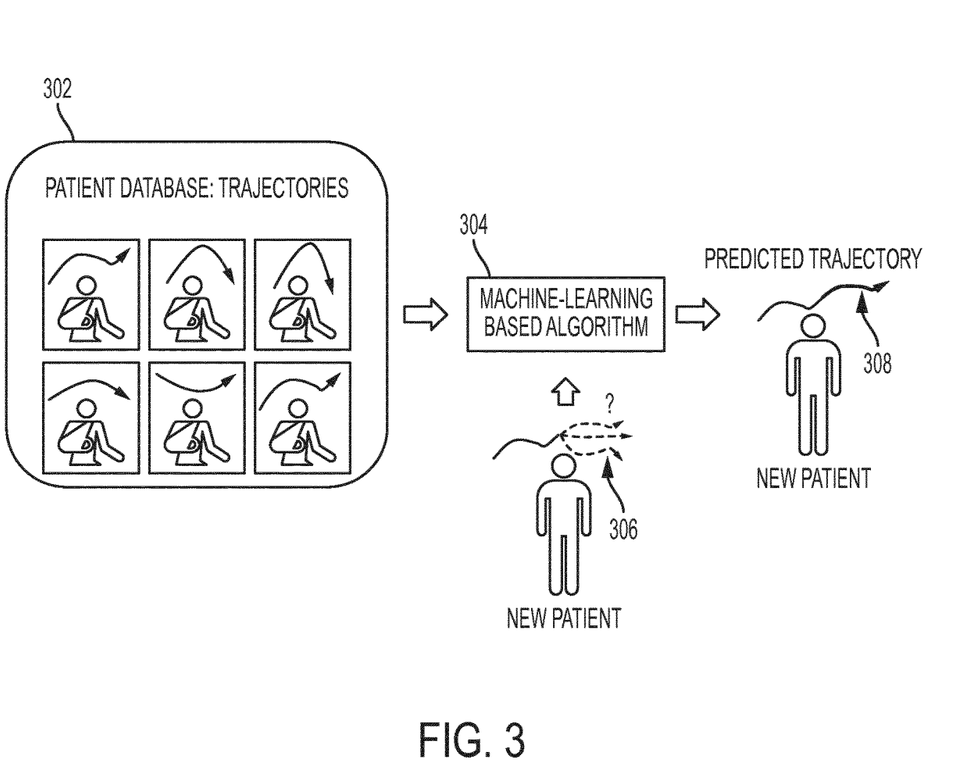
FIG. 3 illustrates predicting a disease trajectory for a patient using a machine-learning based algorithm according to an embodiment of the present invention.

In another embodiment, a machine-learning based algorithm can be used to automatically predict the disease trajectory for the patient based on the state vector of the patient. Using a machine-learning algorithm, a database of disease trajectories may be used to train a machine-learning based classifier to estimate a disease trajectory based on the state variables of a patient. The trained machine-learning based classifier can then be used to estimate a disease trajectory for a new patient based on the state variables for that patient. Any type of supervised, semi-supervised, or unsupervised machine-learning algorithm can be used to train the machine-learning based classifier. For example, machine-learning algorithms, such as support vector machine (SVM), a machine-learning based regressor, deep learning, or deep reinforcement learning, can be used, but the present invention is not limited thereto. FIG. 3 illustrates predicting a disease trajectory for a patient using a machine-learning based algorithm according to an embodiment of the present invention. As shown in FIG. 3, a patient database 302, which included a large number of disease trajectories of different patients is used to train a machine-learning based algorithm 304. Once the machine-learning based algorithm 304 is trained, the known state variables (at a current time or over an initial time period) for a new patient 306 are input to the trained machine-learning based algorithm 304, and the trained machine-learning based algorithm 304 estimates a predicted trajectory 308 for the new patient.

Returning to FIG. 1, at step 106, an optimization is performed to determine an optimal therapy and timing for the patient based on the predicted disease progression. An intervention or therapy, such as drug intervention, surgery, or a device therapy, will cause the system dynamics to change both acutely and over a period of time. Some common examples of interventions include:

Stents, balloon angioplasties, or bypass surgery for various stenosis in coronary, peripheral, cerebral, carotid, aorta, or renal vessels;

Valve replacement and implantation (such as trans catheter aortic valve replacement—TAVR, mitral clip) therapies for the various heart valves;

Heart rhythm devices, such as pacemakers, defibrillators, and ablation therapies, for various heart rhythm disorders;

Structural heart disease therapies, such as left atrial appendage (LAA) closure, atrial-septal defect (ASD), and ventricular septal defect (VSD) closure;

Drug interventions for medical conditions such as heart failure and hypertension;

Oncological interventions for cancer treatment, such as radiation therapy, tumor ablation, chemoembolization, and surgical intervention; and Drug interventions for treating various cancers;

It is to be understood that embodiments of the present invention described herein can be applied to any other kind of intervention as well, and are not limited to only the examples listed above.

Depending on the nature of the intervention, the change in dynamics caused by the intervention may be either gradual or sudden. According to an advantageous embodiment of the present invention, to account for such changes to the dynamics of the state variables, interventions are modeled using hybrid dynamical systems (also referred to as switching systems). In particular, a hybrid dynamical systems approach is used to model the system dynamics, by coupling the continuous dynamics to the discrete intervention events. This can be expressed as:

$$\dot{x}(t) = f_{\sigma(t)}(x(t))$$

where x(t) denotes the continuous dynamics and σ(t) denotes the discrete dynamics that represent the switching signal. The switching used to represent the interventions can be time-dependent or state-dependent. Additionally, the switching can either be intrinsic to the system (i.e., autonomous) or controlled (i.e., the intervention that leads to the switching is designed).

Figure 4:
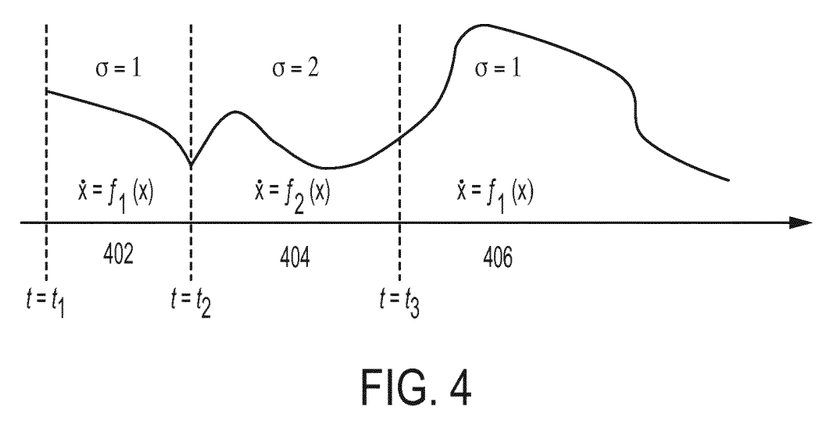
FIG. 4 illustrates modeling of a patient's disease trajectory together with interventions using a time-dependent switching system according to an embodiment of the present invention.

FIG. 4 illustrates modeling of a patient's disease trajectory together with interventions using a time-dependent switching system according to an embodiment of the present invention. The switching system of FIG. 4 includes two switching states represented by σ (i.e., σ=1 and σ=2). The dynamics of the system are different in the different switching states, and are thus characterized by different mathematical functions (i.e., $\dot{x}=f_1(x)$ for σ=1 and $\dot{x}=f_2(x)$ for σ=2). As shown in FIG. 4, the switching is performed at a given time, which can be used to model interventions, such as drug treatment regimens, that are scheduled for a fixed future time. For example, in FIG. 4 $t_2$ can represent a start time for an intervention (such as a drug treatment regimen), and $t_3$ can represent an end time for the intervention. The dynamics of the state variable model are different during the intervention, so the dynamics of the state variable model are characterized by $\dot{x}=f_1(x)$ during the time period 402 before the intervention and the time period 406 after the intervention and characterized by $\dot{x}=f_2(x)$ in the time period 404 during the intervention.

In some cases of drug therapy, the dose and timing of the drug may be based on the value of a particular biomarker, which is one of the state variables. Once the therapy starts or stops, the biomarker itself is subject to change due to the therapy. The interaction between the continuous dynamics of the system variables and the hybrid switching to another regime based on a rule (e.g., biomarker above or below a particular threshold) can be captured using a state-dependent switching system.

Figure 5:
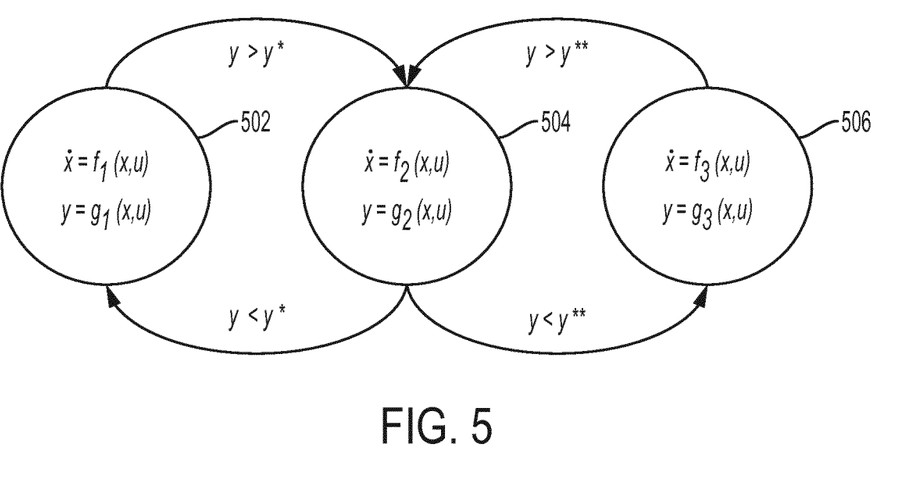
FIG. 5 illustrates a threshold-based state dependent switching system according to an embodiment of the present invention.

FIG. 5 illustrates a threshold-based state dependent switching system according to an embodiment of the present invention. As shown in FIG. 5, the system switched between three discrete dynamics models 502, 504, and 506 based on an output value y for a state variable. The output value y for the state variable is compared to first and second threshold values y* and y**, respectively. When y is less than y*, the dynamics of the system are controlled by dynamics model 502, which can be expressed as $\dot{x}=f_1(x,u)$ and $y=g_1(x,u)$. When y is greater than y* and less than y, the dynamics of the system are controlled by dynamics model 504, which can be expressed as $\dot{x}=f_2(x,u)$ and $y=g_2(x,u)$. When y is greater than y, the dynamics of the system are controlled by dynamics model 506, which can be expressed as $\dot{x}=f_3(x,u)$ and $y=g_3(x,u)$. Such a switching system can be used for modeling medical interventions that are necessitated when a certain rule is satisfied. For example, in the case of aneurysm coiling, the size of the aneurysm is typically used as a surrogate for its risk of rupture. In such cases, when the aneurysm grows above a certain size, the therapy (usually clipping or coiling) is performed. Such a therapy would change the dynamics of the resultant system onto a different trajectory.

By using switching systems (e.g., time-dependent or state-dependent) to model interventions, different types of therapies and different timings for the therapies can be changed to find the type and timing for a therapy that results in the best disease progression for the patient based on the predicted evolution of the state vector. One potential therapy that can be considered is a "do nothing" (or "watchful waiting") therapy, which can be compared to other therapy types and timings.

In order to deliver an effective therapy, several factors may need to be optimized. For example, two factors that need to be optimized are the timing of the therapy and the type of the therapy. Here, it can be assumed that the therapy is delivered as per its instructions (i.e., there is no clinician error). This problem can be posed an optimization problem, where the objective is to maximize the effectiveness of the therapy, and the parameters to be estimated are the timing (t) and the type of the therapy (type):

$$\underset{t, type}{\text{maximize}}\ \text{Effectiveness}\ (t, type)$$

In the above optimization problem, the effectiveness can be a physiological effectiveness of the therapy that can be quantified by the post-intervention state vector or long-term evolution of the state vector of the patient. In a possible implementation, a subset of state variables particular to a specific disease may be used to determine the effectiveness of therapy for that disease. The physiological effectiveness of a therapy is discussed in greater detail below.

The above discussed objective function does not take into account the cost-effectiveness of the therapy. In other possible embodiments, the objective function may be modifies to account for cost-effectiveness by including the cost of the therapy as well:

$$\underset{t, type, cost}{\text{maximize}}\ \text{Effectiveness}\ (t, type, cost)$$

such that type ∈ (type$_1$, type$_2$, ... , type$_N$)

OR $$\underset{t, type}{\text{maximize}}\ \text{Effectiveness}\ (t, type)$$

such that Cost (t, type) < CostLim type ∈ (type$_1$, type$_2$, ... , type$_N$)

In the first of the above embodiments, a multi-numerical optimization problem may be solved by concurrently estimating the optimal timing and type of therapy such that the overall effectiveness is maximized. In this embodiment, the overall effectiveness includes the physiological effectiveness and cost-effectiveness. The relative importance of the physiological effectiveness and the cost-effectiveness to the overall effectiveness can be controlled with weights in the objective function. In the second of the above embodiments, the effectiveness does not take into account cost, but the cost of the therapy selected must be below a cost limit. In this case, the optimization problem is solved by estimating the optimal timing and type of therapy that maximize the physiological effectiveness, while still resulting in a cost that is below the cost limit.

The physiological effectiveness of the therapy can be quantified by the post-intervention state-vector (or the measurement vector that is a subset of state variables) of the patient. While the state vector is a comprehensive set of attributes, all of which may or may not be directly measurable using the devices that are used clinically (e.g., some of these attributes may be extracted from images, or computed by using some physiological computational modeling algorithms, etc.), the measurement vector refers to a subset of state variables that are acquired from clinically performed measurements. The physiological effectiveness can be expressed as:

Physiological Effectiveness=$r[x(t_+), x(t_-)]$, where $t_+$ and $t_-$ represent the post-intervention and pre-intervention time-points, respectively, and r represents a function that calculates the relative change in the patient's state. One example for r can be a distance function that measures the change in the state vector as a result of the therapy. A numerical optimization algorithm can be used to solve the above optimization problems. For example, a gradient-based optimization technique or a gradient-free optimization technique may be employed to solve the above objective problems. In addition algorithms from optimal control theory may also be used to solve the above optimization problems.

Figure 6:
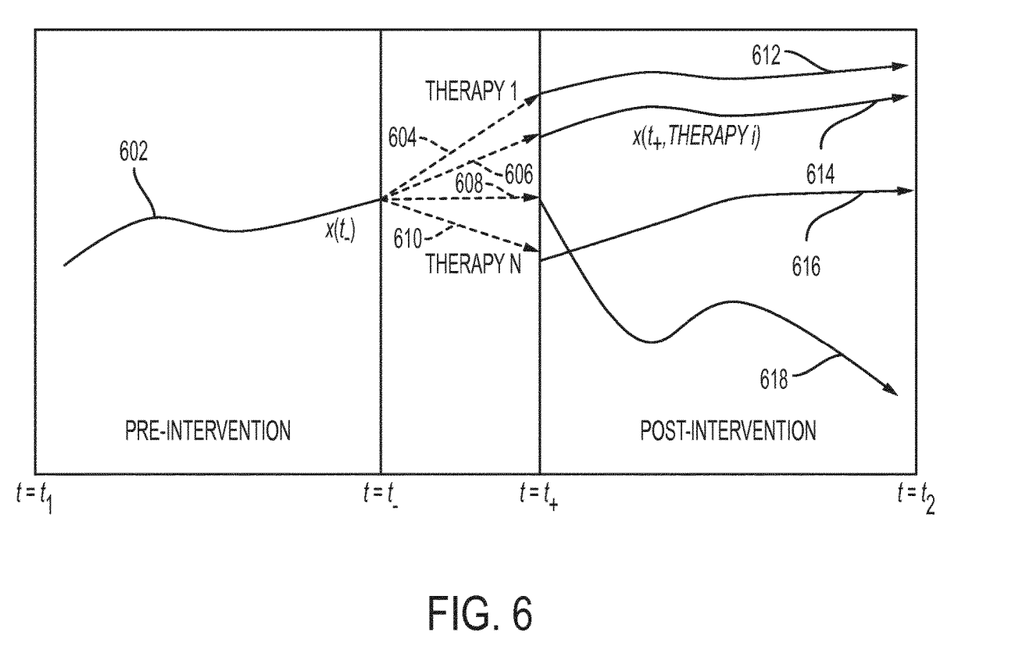
FIG. 6 illustrates modeling the effect of therapies on the disease trajectory of patient for selecting an optimum therapy according to an embodiment of the present invention.

FIG. 6 illustrates modeling the effect of therapies on the disease trajectory of patient for selecting an optimum therapy according to an embodiment of the present invention. A shown in FIG. 6, 602 is the patient's pre-intervention disease trajectory. Various therapies 604, 606, 608, and 610 (Therapy 1-Therapy N) are modeled resulting in respective post-intervention disease trajectories 612, 614, 616, and 618. The physiological effectiveness can be calculated for each therapy by calculating the relative change in the patient's state function at the post-intervention time point $t_+$ as compared to the patient's state function at the pre-intervention time point $t_-$.

In another embodiment, instead of just considering the acute outcome of the intervention (at time $t_+$), the long-term outcome of the therapy can be considered in the optimization problem. In this case, the effectiveness of the therapy can be quantified by predicting the disease progression for an extended amount of time after the therapy and calculating the relative distance between the state vector (or subset of state variables) at some time point after the intervention (for example, $t_2$ in FIG. 6) with the time point before the intervention ($t_-$). Such an approach may also be used to address the issue of hospital readmission penalties that are typically levied by the insurance payers on hospitals. Under such programs, if the outcome for a particular therapy causes the patient to be re-admitted to the hospital for the same issue within a certain number of days (e.g., 30) of discharge, a penalty is levied. This penalty can be modeled into the objective function, as well as during the overall cost minimization.

In another embodiment, instead of considering the time-instant just before the intervention ($t_-$), some other time instant may be used as well. For example, an earlier time (e.g., $t_1$ in FIG. 6) may be used as the basis of comparison for the state vector at the time point after the intervention ($t_+$) or a later time point (e.g., $t_2$ in FIG. 6).

Returning to FIG. 1, at step 108, an optimal therapy recommendation and predicted disease trajectories are output. For example, the optimal therapy type and timing can be output by displaying a recommendation including the optimal therapy type and timing on a display device of a computer system, sending this information in a message (e.g., email), and/or storing the optimal therapy type and timing recommendation on a storage or memory of a computer system. In addition, various predicted disease trajectories for the patient can be output. For example, a predicted disease trajectory for a "do nothing" scenario and predicted disease trajectories for one or more therapy options including different types and timings of therapies can be displayed on a display device of a computer system or stored in a memory or storage of a computer system. These output results can be incorporated in a Clinical Decision Support (CDS) system. These output results can be integrated into an Electronic Medical Record (EMR) system. These output results can be incorporated in a radiologist's reading system at the time when a diagnosis is being mage to inform the radiologist of the potential outcomes the patient might have. These output results can be included in a report that is accessible to the patient so the patient can make informed decisions.

The method of FIG. 1 can be used to predict the progression and optimize therapy selection for many different types of diseases. In an exemplary embodiment, the method of FIG. 1 can be applied for disease progression modeling and therapy optimization for coronary artery disease patients. In coronary artery disease patients, fractional flow reserve (FFR) is currently the gold-standard test for determining the hemodynamic significance of a coronary artery stenosis. The decision for stenting is currently based on a binary FFR cut-off of 0.8, whereby only patients with FFR<0.8 are considered for stent therapy. Recent studies have shown that the FFR value has a continuous relationship with the prognosis of the patient. At the same time, it has been shown that the measurement of FFR immediately after stenting shows an inverse gradient of risk. Such information can be incorporated into the optimization approach described above to characterize the physiological effectiveness of the therapy (based on the state variable of FFR), both for short-term and long-term outcome optimization. For patients with a negative FFR (i.e. FFR>0.80), the clinical recommendation is often to undergo and "optimal medical therapy"—OMT, which refers to the drug dose and regiment tailored for an individual. Such drug therapies can also be analyzed in the same framework that we have presented.

As described above, various state variables may be determined from medical imaging data using imaging processing techniques. In a possible embodiment, depending on the state-vector at a given time, a medical imaging test may be ordered for a specific purpose, but not for determining the entire function of the patient.

Figure 7:
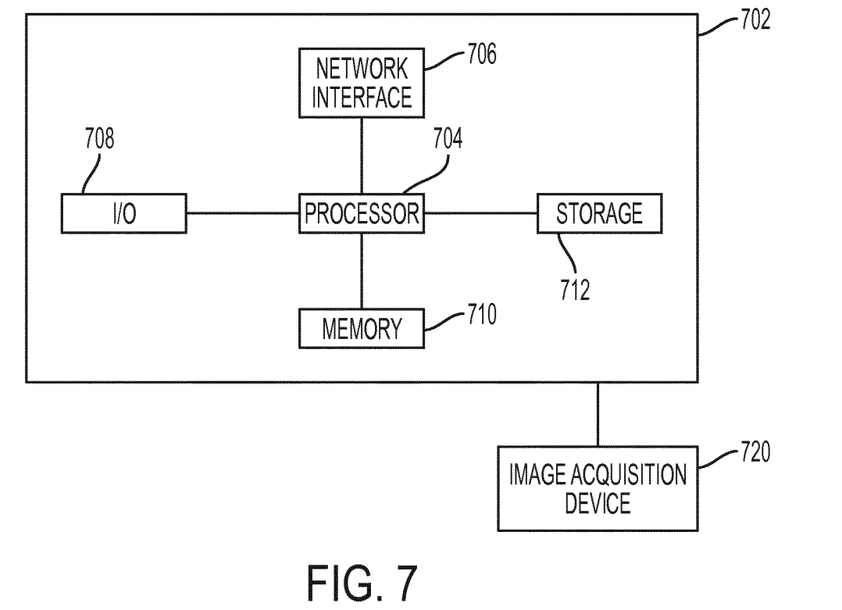
FIG. 7 is a high-level block diagram of a computer capable of implementing the present invention.

The above-described methods for automated disease progression modeling and therapy optimization may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIG. 1 may be defined by the computer program instructions stored in the memory 710 and/or storage 712 and controlled by the processor 704 executing the computer program instructions. An image acquisition device 720, such as a CT scanning device, MR scanning device, Ultrasound device, etc., can be connected to the computer 702 to input image data to the computer 702. It is possible to implement the image acquisition device 720 and the computer 702 as one device. It is also possible that the image acquisition device 720 and the computer 702 communicate wirelessly through a network. In a possible embodiment, the computer 702 may be located remotely with respect to the image acquisition device 720 and the method steps are performed as part of a server or cloud based service. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). One skilled in the art will recognize that an implementation of an actual computer could contain other components as well, and that FIG. 7 is a high level representation of some of the components of such a computer for illustrative purposes.

The above-described methods for disease progression modeling and therapy optimization may be implemented using computers operating in a client-server relationship. Typically, in such a system, the client computers are located remotely from the server computer and interact via a network. The client-server relationship may be defined and controlled by computer programs running on the respective client and server computers.

The above-described methods for disease progression modeling and therapy optimization may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 1. Certain steps of the methods described herein, including one or more of the steps of FIG. 1, may be performed by a server or by another processor in a network-based cloud-computing system. Certain steps of the methods described herein, including one or more of the steps of FIG. 1, may be performed by a client computer in a network-based cloud computing system. The steps of the methods described herein, including one or more of the steps of FIG. 1, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for disease progression modeling and therapy optimization for a patient, comprising:
   modeling a condition of the patient using a state-variable model in which a plurality of state variables in a state vector represent a plurality of characteristics of the patient;
   predicting disease progression for the patient based on the state variables of the patient; and
   performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables,
   wherein performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables comprises:
      adjusting the predicted disease progression to model the therapy types and timings, and
      selecting the optimal therapy type and the optimal therapy timing to maximize an effectiveness of the therapy;
   wherein selecting the optimal therapy type and the optimal therapy timing to maximize an effectiveness of the therapy comprises:
      selecting the optimal therapy type and the optimal therapy timing to maximize a physiological effectiveness of the therapy, wherein the physiological effectiveness of the therapy is measured by calculating a relative change between values of one or more state variables of the patient at a time point before the therapy and predicted values of the one or more state variables of the patient at a time point after the therapy; and
   wherein the physiological effectiveness of the therapy is penalized if the state variables of the patient indicate that the patient would be re-admitted to a hospital within a predetermined amount of time after the therapy.

2. The method of claim 1, wherein the plurality of state variables include results of plurality of diagnostic tests.

3. The method of claim 1, wherein the plurality of state variables includes measurements from a plurality of biological scales.

4. The method of claim 1, wherein modeling a condition of the patient using a state-variable model in which a plurality of state variables in a state vector represent a plurality of characteristics of the patient comprises:
   determining values for one or more of the plurality of state variables from medical imaging data of the patient.

5. The method of claim 1, wherein modeling a condition of the patient using a state-variable model in which a plurality of state variables in a state vector represent a plurality of characteristics of the patient comprises:
   estimating dynamics of the state variables using a dynamic system identification algorithm.

6. The method of claim 1, wherein predicting disease progression for the patient based on the state variables of the patient comprises:
   predicting a disease trajectory for the patient by determining a typical disease trajectory for a sub-group of patients in a disease trajectory database, wherein the sub-group of patients in the disease trajectory database is defined based on values of one or more of the state variables of the patient.

7. The method of claim 1, wherein predicting disease progression for the patient based on the state variables of the patient comprises:
   grouping disease trajectories in a disease trajectory database into a plurality of clusters using a trajectory clustering algorithm;
   determining a most similar cluster to the patient of the plurality of clusters based on the state variables of the patient; and
   determining a predicted disease trajectory of the patient based on an average disease trajectory of the most similar cluster to the patient.

8. The method of claim 1, wherein predicting disease progression for the patient based on the state variables of the patient comprises:
   predicting a disease trajectory by the patient based on the state variables of the patient using a machine-learning based classifier trained based on a database of disease trajectories using a machine-learning algorithm.

9. The method of claim 1, wherein the hybrid dynamical system switches between the discrete models based on the therapy type and timing being modeled.

10. The method of claim 1, wherein the hybrid dynamical system switches between the discrete models in response to the value of the one of the state variables being lower or higher than one or more thresholds.

11. The method of claim 1, wherein selecting the optimal therapy type and the optimal therapy timing to maximize a physiological effectiveness of the therapy comprises:
   selecting the optimal therapy type and the optimal therapy timing to maximize the physiological effectiveness of the therapy subject to a constraint that a cost of the optimal therapy type and the optimal therapy timing selected is less than a specified cost limit.

12. An apparatus for disease progression modeling and therapy optimization for a patient, comprising:
   means for modeling a condition of the patient using a state-variable model in which a plurality of state variables in a state vector represent a plurality of characteristics of the patient;
   means for predicting disease progression for the patient based on the state variables of the patient; and
   means for performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables;
   wherein the means for performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables comprises:
      means for adjusting the predicted disease progression to model the therapy types and timings, and means for selecting the optimal therapy type and the optimal therapy timing to maximize an effectiveness of the therapy;
wherein the means for selecting the optimal therapy type and the optimal therapy timing to maximize an effectiveness of the therapy comprises:
selecting the optimal therapy type and the optimal therapy timing to maximize a physiological effectiveness of the therapy, wherein the physiological effectiveness of the therapy is measured by calculating a relative change between values of one or more state variables of the patient at a time point before the therapy and predicted values of the one or more state variables of the patient at a time point after the therapy; and
wherein the physiological effectiveness of the therapy is penalized if the state variables of the patient indicate that the patient would be re-admitted to a hospital within a predetermined amount of time after the therapy.

13. The apparatus of claim 12, wherein the means for predicting disease progression for the patient based on the state variables of the patient comprises:
means for predicting a disease trajectory for the patient by determining a typical disease trajectory for a sub-group of patients in a disease trajectory database, wherein the sub-group of patients in the disease trajectory database is defined based on values of one or more of the state variables of the patient.

14. The apparatus of claim 12, wherein the means for predicting disease progression for the patient based on the state variables of the patient comprises:
means for grouping disease trajectories in a disease trajectory database into a plurality of clusters using a trajectory clustering algorithm;
means for determining a most similar cluster to the patient of the plurality of clusters based on the state variables of the patient; and
means for determining a predicted disease trajectory of the patient based on an average disease trajectory of the most similar cluster to the patient.

15. The apparatus of claim 12, wherein the means for predicting disease progression for the patient based on the state variables of the patient comprises:
means for predicting a disease trajectory by the patient based on the state variables of the patient using a machine-learning based classifier trained based on a database of disease trajectories using a machine-learning algorithm.

16. The apparatus of claim 12, wherein
the hybrid dynamical system switches between the discrete models based on the therapy type and timing being modeled.

17. A non-transitory computer readable medium storing computer program instructions for disease progression modeling and therapy optimization for a patient, the computer program instructions when executed by a processor cause the processor to perform operations comprising:
modeling a condition of the patient using a state-variable model in which a plurality of state variables in a state vector represent a plurality of characteristics of the patient;
predicting disease progression for the patient based on the state variables of the patient; and
performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables;
wherein performing an optimization to determine an optimal therapy type and an optimal therapy timing for the patient based on the predicted disease progression for the patient by modeling therapy types and timings using a hybrid dynamical system that switches between discrete models based on a value of one of the plurality of state variables comprises:
adjusting the predicted disease progression to model the therapy types and timings, and
selecting the optimal therapy type and the optimal therapy timing to maximize an effectiveness of the therapy;
wherein selecting the optimal therapy type and the optimal therapy timing to maximize an effectiveness of the therapy comprises:
selecting the optimal therapy type and the optimal therapy timing to maximize a physiological effectiveness of the therapy, wherein the physiological effectiveness of the therapy is measured by calculating a relative change between values of one or more state variables of the patient at a time point before the therapy and predicted values of the one or more state variables of the patient at a time point after the therapy; and
wherein the physiological effectiveness of the therapy is penalized if the state variables of the patient indicate that the patient would be re-admitted to a hospital within a predetermined amount of time after the therapy.

18. The non-transitory computer readable medium of claim 17, wherein predicting disease progression for the patient based on the state variables of the patient comprises:
predicting a disease trajectory for the patient by determining a typical disease trajectory for a sub-group of patients in a disease trajectory database, wherein the sub-group of patients in the disease trajectory database is defined based on values of one or more of the state variables of the patient.

19. The non-transitory computer readable medium of claim 17, wherein predicting disease progression for the patient based on the state variables of the patient comprises:
grouping disease trajectories in a disease trajectory database into a plurality of clusters using a trajectory clustering algorithm;
determining a most similar cluster to the patient of the plurality of clusters based on the state variables of the patient; and
determining a predicted disease trajectory of the patient based on an average disease trajectory of the most similar cluster to the patient.

20. The non-transitory computer readable medium of claim 17, wherein predicting disease progression for the patient based on the state variables of the patient comprises:
predicting a disease trajectory by the patient based on the state variables of the patient using a machine-learning based classifier trained based on a database of disease trajectories using a machine-learning algorithm.

21. The non-transitory computer readable medium of claim 17, wherein
the hybrid dynamical system switches between the discrete models based on the therapy type and timing being modeled.

* * * * *